United States Patent
Horna Tomás et al.

(10) Patent No.: US 12,275,930 B2
(45) Date of Patent: Apr. 15, 2025

(54) DISPOSABLE CARTRIDGE COOPERATING WITH A PLATFORM FOR A SYSTEM AND INSTALLATION FOR MONITORING AND CONTROLLING FLUIDS

(71) Applicant: AGLARIS LTD, Hertfordshire (GB)

(72) Inventors: David Horna Tomás, Hertfordshire (GB); Miquel Costa Ferrando, Hertfordshire (GB); Jorge Aranda Hernández, Hertfordshire (GB); Mireia Ruiz Maymó, Hertfordshire (GB); Carlos Julià Figueras, Hertfordshire (GB)

(73) Assignee: AGLARIS LTD, Hertfordshire (GB)

( * ) Notice: Subject to any disclaimer, the term of this patent is extended or adjusted under 35 U.S.C. 154(b) by 953 days.

(21) Appl. No.: 17/048,740

(22) PCT Filed: Apr. 17, 2019

(86) PCT No.: PCT/EP2019/059979
§ 371 (c)(1),
(2) Date: Oct. 19, 2020

(87) PCT Pub. No.: WO2019/202024
PCT Pub. Date: Oct. 24, 2019

(65) Prior Publication Data
US 2021/0261904 A1 Aug. 26, 2021

(30) Foreign Application Priority Data
Apr. 19, 2018 (EP) .................................... 18168268

(51) Int. Cl.
*C12M 1/36* (2006.01)
*C12M 1/00* (2006.01)
(Continued)

(52) U.S. Cl.
CPC ............. *C12M 41/48* (2013.01); *C12M 23/28* (2013.01); *C12M 23/42* (2013.01); *C12M 41/26* (2013.01);
(Continued)

(58) Field of Classification Search
None
See application file for complete search history.

(56) References Cited

U.S. PATENT DOCUMENTS

2006/0257941 A1  11/2006  McDevitt et al.
2012/0244609 A1   9/2012  Selker et al.
(Continued)

FOREIGN PATENT DOCUMENTS

WO   2006/119622 A1   11/2006
WO   2010/061866 A2    6/2010
WO   2014/150832 A2    9/2014

OTHER PUBLICATIONS

Talaei et al., Enzyme SU-8 microreactors: simple tools for cell-culture monitoring, 2015, Microfluid Nanofluid, 19:351-361 (Year: 2015).*
(Continued)

*Primary Examiner* — Holly Kipouros
(74) *Attorney, Agent, or Firm* — Kramer & Amado, P.C.

(57) ABSTRACT

The invention is comprised among control devices for controlling and monitoring fluids and for the handling thereof. The invention relates to the integration of these control devices in a disposable cartridge cooperating with a platform for a system for monitoring and controlling a fluid. Specifically, the invention relates to a disposable cartridge and a platform, cooperating with one another, for a system for monitoring and controlling the state of a fluid, wherein the cartridge comprises at least two sensors. The invention also relates to a system and installation for monitoring and
(Continued)

controlling the state of a fluid. More particularly, the present invention is intended for monitoring and controlling the state of a cell culture.

10 Claims, 9 Drawing Sheets

(51) Int. Cl.
*C12M 1/34* (2006.01)
*C12M 3/00* (2006.01)

(52) U.S. Cl.
CPC ............ *C12M 41/32* (2013.01); *C12M 41/34* (2013.01); *C12M 41/46* (2013.01)

(56) References Cited

U.S. PATENT DOCUMENTS

| | | | | |
|---|---|---|---|---|
| 2013/0244241 | A1* | 9/2013 | Carrera Fabra | B01L 3/50273 435/7.1 |
| 2015/0247794 | A1* | 9/2015 | Olesberg | C12Q 3/00 250/339.07 |
| 2016/0356999 | A1* | 12/2016 | Fine | G02B 21/0008 |
| 2017/0037357 | A1* | 2/2017 | Cattaruzzi | C12M 41/48 |
| 2020/0009557 | A1* | 1/2020 | Frigard | B01D 15/10 |

OTHER PUBLICATIONS

International Search Report issued Jul. 11, 2019.

* cited by examiner

DISPOSABLE CARTRIDGE COOPERATING WITH A PLATFORM FOR A SYSTEM AND INSTALLATION FOR MONITORING AND CONTROLLING FLUIDS

OBJECT OF THE INVENTION

The invention is comprised among control devices for controlling and monitoring fluids and for the handling thereof. The invention relates to the integration of these control devices in a disposable cartridge cooperating with a platform for a system for monitoring and controlling a fluid. Specifically, the invention relates to a disposable cartridge and a platform, cooperating with one another, for a system for monitoring and controlling the state of a fluid, wherein the cartridge comprises at least two sensors. The invention also relates to a system and an installation for monitoring and controlling the state of a fluid. More particularly, the present invention is intended for monitoring and controlling the state of a cell culture.

BACKGROUND OF THE INVENTION

Bioreactors intended for cell culture having a series of systems and/or devices and for controlling and monitoring the state of the cell culture throughout same are known in the state of the art. Bioreactors having, on one hand, optical systems for controlling pH, $CO_2$ and $O_2$ (optical sensors), and on the other hand, enzyme systems for controlling glucose and lactate (enzyme sensors, biomass sensors, etc.) are known today. These systems are contemplated as systems which are each independently connected with the main circuit of the bioreactor. In addition to said systems, these bioreactors also have electronic hardware independent of the sensor systems, but connected thereto.

These known bioreactors have the drawback that each sensor is independent of the others, and the connections existing between each of the sensors and the culture system are complex and hard to make. Furthermore, the sensors must not interfere with one another and with the cell culture since said cultures must remain sterile and contaminant-free. Therefore, current bioreactors present a technical problem of numerous interventions and handling by each sensor in an independent manner before and during cell culture. This increases the risks of culture contamination. Likewise, since each sensor is independent of the others and has its own software, the integration of each sensor with its software is complex and complicates the control of said sensors through different software.

In addition to cell culture systems or bioreactors, systems for handling fluids having the same drawbacks as said cell culture systems are also present in the state of the art. Some of these examples of the handling of fluids are systems or reactors for chemical processes intended for the pharmaceutical industry, biotechnology industry and medical industry, among others.

To solve these technical problems, a device or system integrating all the sensors required for controlling fluids, more particularly cell culture, has been developed so that it is therefore the only system or device that is connected with the main circuit of the fluid handling system or fluid handling receptacle, more particularly the bioreactor in the case of cell cultures, thereby reducing the number of interventions and handling, and accordingly preventing the risk of contamination.

DESCRIPTION OF THE INVENTION

The present invention proposes a solution to the preceding problems by means of a disposable cartridge for cooperating with a platform according to claim 1, a platform for cooperating with the cartridge, a system for monitoring and controlling the state of a cell culture, and an installation for cell culture. The dependent claims define the preferred embodiments of the invention.

A first inventive aspect provides a disposable cartridge for cooperating with a platform for a system for monitoring and controlling the state of at least a cell culture, characterized in that it comprises:
- a duct network comprising at least one fluid inlet and fluid outlet, this duct network being configured for circulating at least one fluid therein,
- a first sensor connected to the duct network, the first sensor being configured for measuring at least a first fluid parameter,
- a second sensor connected to the duct network, the second sensor being configured for measuring at least a second fluid parameter regardless of the first sensor, the second fluid parameter being different from the first fluid parameter, and
- flow control means for controlling the flow of fluid circulating through the duct network, wherein
the first sensor and second sensor are configured for connecting with at least one processing means of the platform, respectively, and
the fluid to be circulated in the duct network is a medium, or cells suspended in a medium, or a sample of any of the above, and the medium is a liquid medium and/or a culture medium.

Throughout this document, "cartridge" will be understood as a device formed by a series of components, including, among others, one or more sensors controlling the state of at least one fluid coming from a fluid handling receptacle and circulating through the duct network. This cartridge is disposable, which means that once it is used and/or a predetermined experimental work cycle has ended, the cartridge can be disposed of and replaced with another one.

Advantageously, the present disposable cartridge is readily integrated in any system for handling fluids. Furthermore, the fact that the cartridge which cooperates with a platform may be a disposable cartridge, and may therefore be replaced with a new one that will cooperate with the same platform as the preceding one, allows simply coupling and/or connecting the new cartridge to the platform in order for said new cartridge and the platform to start cooperating with one another in a simple manner and without performing new interventions in the fluid. Once this new disposable cartridge is connected to the platform, it can furthermore be connected to a fluid handling receptacle through the fluid inlet and the fluid outlet comprised in the duct network of the corresponding new disposable cartridge.

The duct network is formed by a plurality of ducts and/or tubes that can be in fluid communication with one another. In turn, this duct network comprises a fluid inlet and a fluid outlet through which said duct network is in fluid communication with the interior of a fluid handling receptacle where handling of said fluids is carried out.

Throughout the document, "connecting" will be understood as two or more components coming into communication with one another. For example, the present disposable cartridge comprises sensors configured for coming into communication, respectively, with the processing means of the platform, i.e., the sensors can connect with the processing means.

Each of the sensors defined in this particular embodiment measures different parameters of a fluid that circulates through the interior of the duct network and comes from one or more fluid handling receptacles where these fluids are handled.

These sensors work independently of one another, although they are contained in one and the same cartridge, which advantageously reduces the number of interventions and handling with the fluid handling receptacle to a minimum; and the risk of contamination is accordingly reduced.

As a result of this integration of sensors and a suitable data analysis, the handling of fluids and even the quality of the handled fluid can advantageously be controlled depending on the sensors that are included in the disposable cartridge.

Furthermore, the sensors integrated in the disposable cartridge are configured for connecting, independently of one another, with the processing means housed in the platform with which the disposable cartridge cooperates. Therefore, once the cartridge finishes the experimental work cycle, it will be replaced with a new one that will be configured so that the sensors comprised therein connect with the processing means of the same platform, respectively, and so in processes for controlling and monitoring the state of a fluid, changing the cartridge would be enough to enable taking a new series of measurements.

In a particular embodiment, the disposable cartridge comprises at least one receptacle connected to the duct network, the at least one receptacle being configured for housing fluids therein. In another particular embodiment, the at least one receptacle is furthermore configured for receiving fluids therein and/or releasing fluids from its interior along the duct network. More particularly, the at least one receptacle is configured for releasing fluids, preferably towards at least one of the sensors.

In a particular embodiment, the disposable cartridge comprises a residue receptacle connected to the duct network, the residue receptacle being configured for housing therein fluids coming from at least one of the sensors; more particularly for housing therein fluids coming from the second sensor; and it further comprises:
  a cleaning receptacle connected to the duct network, the cleaning receptacle being configured for releasing a cleaning liquid from its interior towards at least one of the sensors along the duct network; preferably towards the second sensor, or
  a calibration receptacle connected to the duct network, the calibration receptacle being configured for housing therein calibration fluids that can be released along the duct network, or
  a combination of the above.

The residue receptacle advantageously allows storing therein fluids circulating through the duct network, also fluids coming from the at least one sensor, and/or cleaning liquid or calibration fluids coming from the cleaning receptacle or the calibration receptacle, respectively.

Furthermore, the present disposable cartridge integrating sensors of different types advantageously allows the automatic washing thereof, as a result of the cleaning liquid, after each measurement taken by the sensors or when the user considers it necessary.

The calibration receptacle is a receptacle comprising a calibration liquid suitable for calibrating at least one of the sensors integrated in the cartridge. Sensors which must be calibrated before they start taking measurements are present in some cases. In particular, said calibration liquid is made to flow several times through the sensors of interest to provide an indication to these sensors of the concentration value considered suitable, so when a sensor detects an unknown fluid concentration of the fluid to be measured, said sensor can then measure same. A calibration curve with several measurements having a known value is plotted with this calibration liquid, such that when an unknown value goes through the sensor, a measurement is obtained which is compared with the calibration curve for obtaining the value that is being measured.

In a more particular embodiment, the duct network comprises a plurality of ducts which are connected with one another and/or with the fluid inlet and/or fluid outlet of the disposable cartridge. Furthermore, more particularly, one or more sensors can be connected on each duct comprised in this duct network.

Each sensor works independently with respect to the other sensors.

In a particular embodiment, the duct network comprises:
  a first duct arranged between the fluid inlet and the fluid outlet, and
  a second duct configured for being in fluid communication with the fluid inlet,
  wherein the first sensor is connected to the first duct, and the second sensor is connected to the second duct.

According to this duct network distribution, each sensor works independently, not only due to the fact that each sensor is configured for measuring different parameters, but also due to the fact that each sensor is connected and/or arranged in a different duct. Therefore, it is understood that for the embodiment in which the fluid only circulates through one of the ducts, measurements could then only be taken with the sensor connected to said duct.

In a more particular embodiment, the first duct will be understood as the main duct through which fluid coming from a fluid handling receptacle circulates, said fluid in turn being introduced back into the interior of said fluid handling receptacle. This is because the first duct is connected at one of the ends thereof to the fluid inlet and at the other end to the fluid outlet of the duct network. However, through the second duct can flow a fluid coming from the fluid inlet that, nevertheless, does not have to be conveyed back into the interior of the fluid handling receptacle.

In a more particular embodiment, the second duct comprises three ends, one being connected to the fluid inlet, another one being connected to the cleaning receptacle, and the last end being connected to the residue receptacle.

In a more particular embodiment, the second duct is configured for being in fluid communication with the fluid inlet of the duct network through the first duct.

In other words, the second duct is connected to the first duct such that it is in fluid communication with the fluid inlet through said first duct. With this configuration, advantageously, the disposable cartridge only needs to be connected to the fluid handling receptacle through the fluid inlet and the fluid outlet of the duct network without having to increase the number of connections with the interior of said fluid handling receptacle.

In a particular embodiment, the flow control means for controlling the flow of fluid comprise:
  at least one pump connected to the duct network and adapted for controlling the flow of fluid circulating through the duct network, or
  at least one valve connected to the duct network and configured for regulating the passage of fluid through the duct network, or
  a combination of the above.

In a particular embodiment, the fluid flow control means comprise:

a first pump connected to the duct network and adapted for controlling the flow of fluid circulating through this duct network, and a second pump connected to the duct network and adapted for controlling the flow of cleaning liquid coming from the cleaning receptacle.

In another particular embodiment, the fluid flow control means comprise:

a third pump connected to the duct network and adapted for controlling the flow of cleaning liquid coming from the cleaning receptacle and for taking fluid samples from the first duct, a first valve located in the duct network and configured for regulating the passage of fluid through the duct network, and a second valve located in the duct network and configured for regulating the passage of cleaning liquid coming from the cleaning receptacle through the duct network.

In a more particular embodiment, the pumps are peristaltic micropumps and are configured for driving the fluid and/or cleaning liquid through the ducts.

The peristaltic micropumps are advantageously configured for acting as a pump or a pinch valve. Furthermore, micropumps of this type may be disposable.

In another more particular embodiment, the valves are tube pinch valves. Advantageously, this type of valve acts such that it does not interfere with the tube or duct.

In a particular embodiment, the disposable cartridge further comprises a pump for driving the fluid through the fluid inlet. This pump for driving an inflow fluid is mainly formed by a motor, which is understood as the actuator, and a head with an inlet and an outlet that connect with ducts of the actual duct network of the disposable cartridge. In particular, the pump motor is located in the platform and the pump heads, the inlet and outlet of which are connected with the duct network, are part of the disposable cartridge itself. In a particular embodiment in which the disposable cartridge is coupled to the platform, said head of the disposable cartridge is connected and/or coupled to the motor arranged in the platform. In a preferred embodiment, the pump for driving the inflow fluid is a peristaltic pump.

In a particular embodiment, at least one of the two sensors, preferably the first sensor is an optical sensor.

In another particular embodiment, at least one of the sensors is an optical sensor for optical microscopy analysis.

More particularly, at least one of the sensors is an optical, pH, $O_2$ and/or $CO_2$ sensor.

In a particular embodiment, at least one of the sensors, preferably the second sensor, is an enzyme sensor; and more particularly, at least one of the sensors is a glucose, glutamine and/or lactate enzyme sensor.

Advantageously, each of the sensors may take measurements simultaneously or independently of one another.

In a particular embodiment, the disposable cartridge further comprises a temperature sensor connected to the duct network. This temperature sensor is configured for measuring the temperature at which the measurements are taken and/or the temperature of the fluid circulating through the duct network.

In a particular embodiment, the disposable cartridge further comprises a biomass sensor connected to the duct network, this biomass sensor being configured for calculating the biomass or cell growth in real time, when measurements are being taken, when the fluid is understood as a culture medium coming from a cell culture system or a cell culture chamber.

In a particular embodiment, the disposable cartridge further comprises a spectroscopic and/or spectrometric sensor connected to the duct network.

In a second inventive aspect, the invention provides a platform for cooperating with the disposable cartridge of any of the embodiments of the first inventive aspect for a system for monitoring and controlling the state of at least a cell culture, the platform being configured for being coupled with the disposable cartridge, characterized in that the platform comprises:

processing means configured for controlling at least the first and second sensor of the disposable cartridge, respectively, interconnection means adapted for centralizing the electrical connections of the sensors of the disposable cartridge, of at least one of the fluid flow control means, and of an external electronic data treatment system, wherein the fluid t to be circulated in the duct network of the disposable cartridge is a medium, or cells suspended in a medium, or a sample of any of the above, and the medium is a liquid medium and/or a culture medium.

In a particular embodiment, the interconnection means are furthermore adapted for centralizing the electrical connections of the motors of the micropumps (flow control means) arranged in the disposable cartridge.

In a particular embodiment, when the disposable cartridge comprises a pump for driving an inflow fluid, the platform further comprises a pump motor configured for being connected or coupled to a pump head arranged in the disposable cartridge.

In a particular embodiment, the platform comprises a housing suitable for housing therein the disposable cartridge such that it is coupled inside the platform. The platform has dimensions such that it can accommodate the disposable cartridge therein. Advantageously, full control over the fluid coming from the fluid handling receptacle would be obtained through the present disposable cartridge in cooperation with the platform.

In a third inventive aspect, the invention proposes a system for monitoring and controlling the state of a cell culture, characterized in that it comprises:

a disposable cartridge according to any of the embodiments of the first inventive aspect, and a platform according to the second inventive aspect, wherein the disposable cartridge cooperates with the platform for monitoring and controlling the state of the at least a cell culture, and a fluid to be circulated in the duct network of the disposable cartridge is a medium, or cells suspended in a medium, or a sample of any of the above, and the medium is a liquid medium and/or a culture medium.

The disposable cartridge is configured for being coupled with the platform with which it cooperates, such that the fluid inlet and the fluid outlet of the duct network of said disposable cartridge would be accessible from outside the platform.

In a fourth inventive aspect, the invention provides an installation for monitoring and controlling the state of the at least a cell culture, comprising:

at least receptacle cell culture chamber adapted for handling fluids therein, a system according to the third inventive aspect, and an external electronic data treatment system, wherein the electronic data treatment system is configured for treating data of the at least one of the sensors (5, 6) of the disposable cartridge (1) and furthermore for being connected to the interconnection means (21) of the platform (2) of the system; the inlet and the outlet of the duct network of the disposable cartridge of the system are configured for being in fluid communication with the interior of the cell culture chamber, and a fluid to be circulated in the duct network of the disposable cartridge is a medium, or cells suspended in a medium, or a sample of any of the above, and the medium is a liquid medium and/or a culture medium.

In a particular embodiment, the installation comprises flow control means for controlling the flow of fluid entering and leaving the at least one fluid handling receptacle. The fluid handling receptacle is understood as a container in which the fluids are handled according to the interest of the user, for example, a container or chamber in which chemical and/or biotechnological processes are carried out.

The flow control means for controlling the flow of fluid entering and leaving the at least one fluid handling receptacle work continuously regardless of whether or not the sensors of the disposable cartridge are taking measurements. In other words, these control means are always active. More particularly, these control means are located after or before the disposable cartridge, i.e., between the fluid handling receptacle and the inlet where the flow of fluid enters the disposable cartridge, or between the outlet where the flow of fluid leaves the cartridge and the fluid handling receptacle.

In a particular embodiment, the flow control means for controlling the flow of fluid entering and leaving the fluid handling receptacle are a peristaltic pump. Through this pump, the installation works under perfusion conditions.

The external electronic data treatment system is understood as an electronic system for treating and processing information or data from the measurements carried out by the sensors. In a particular embodiment, the external electronic data treatment system is furthermore in charge of sending instructions to the system so that, for example, the sensors and/or the flow control means start operating or are activated.

In this particular embodiment, the fluid comes from a cell culture chamber and the system is a cell culture system or a bioreactor. In other words, the installation is an installation for monitoring and controlling the state of a cell culture, particularly of the culture medium, of the cells suspended in the culture medium, among others. As a result of this installation, cell growth and even cell quality can be controlled depending on the sensors that are included in the disposable cartridge of the system of said installation.

All the features and/or steps of methods described in this specification (including the claims, description and drawings) can be combined in any combination, with the exception of combinations of such mutually exclusive features.

DESCRIPTION OF THE DRAWINGS

These and other features and advantages of the invention will be more clearly understood based on the following detailed description of a preferred embodiment given only by way of illustrative and non-limiting example in reference to the attached drawings.

DETAILED DESCRIPTION OF THE INVENTION

FIGS. 1A to 9 show several examples of a system for monitoring and controlling the state of a cell culture in which the fluid handling receptacle (22) will be understood as a cell culture chamber and the fluid as a culture medium, or cells suspended in a culture medium, or a sample of any of the above, or a cleaning liquid, or any combination of the above. This system comprises a disposable cartridge (1) and a platform (2) both configured for cooperating with one another.

Figure 1A:
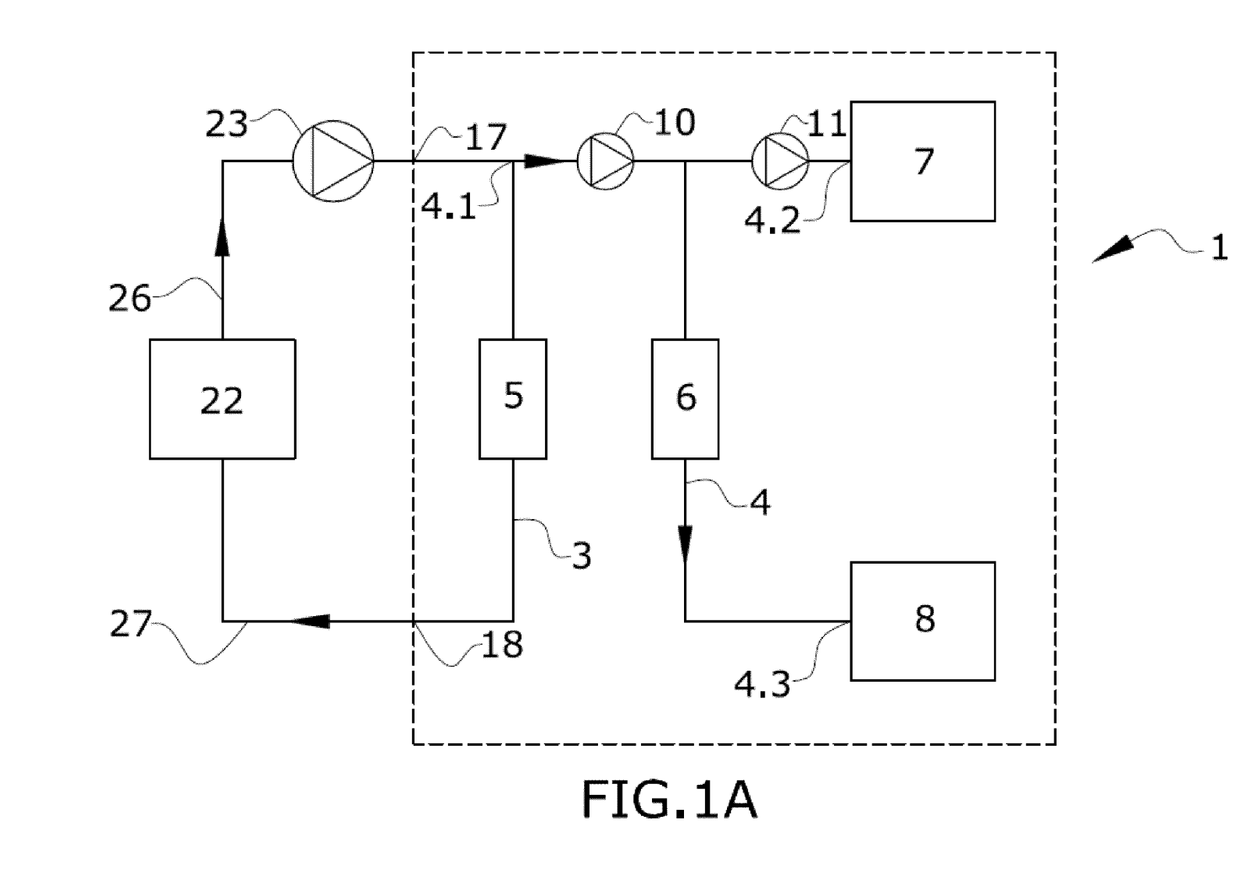
FIG. 1A shows a particular schematic example of the disposable cartridge according to a particular embodiment of the present invention.
Figure 1B:
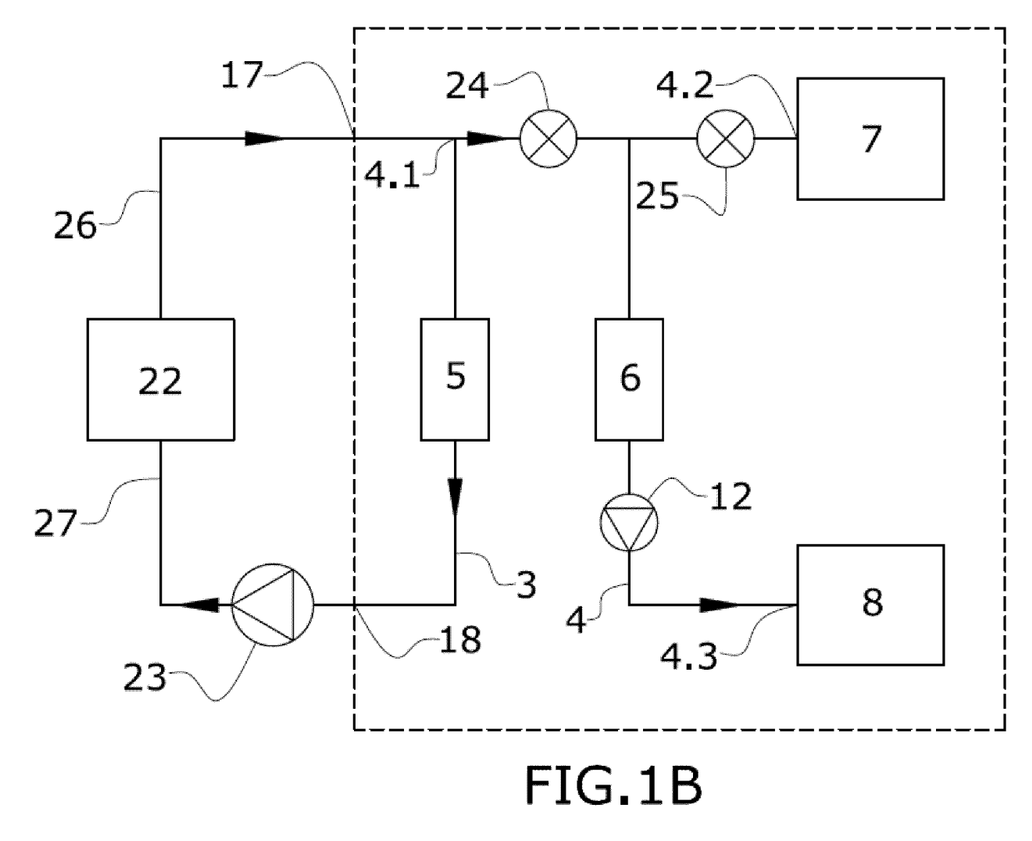
FIG. 1B illustrates a particular schematic example of the disposable cartridge according to another particular embodiment of the present invention.
Figure 2:
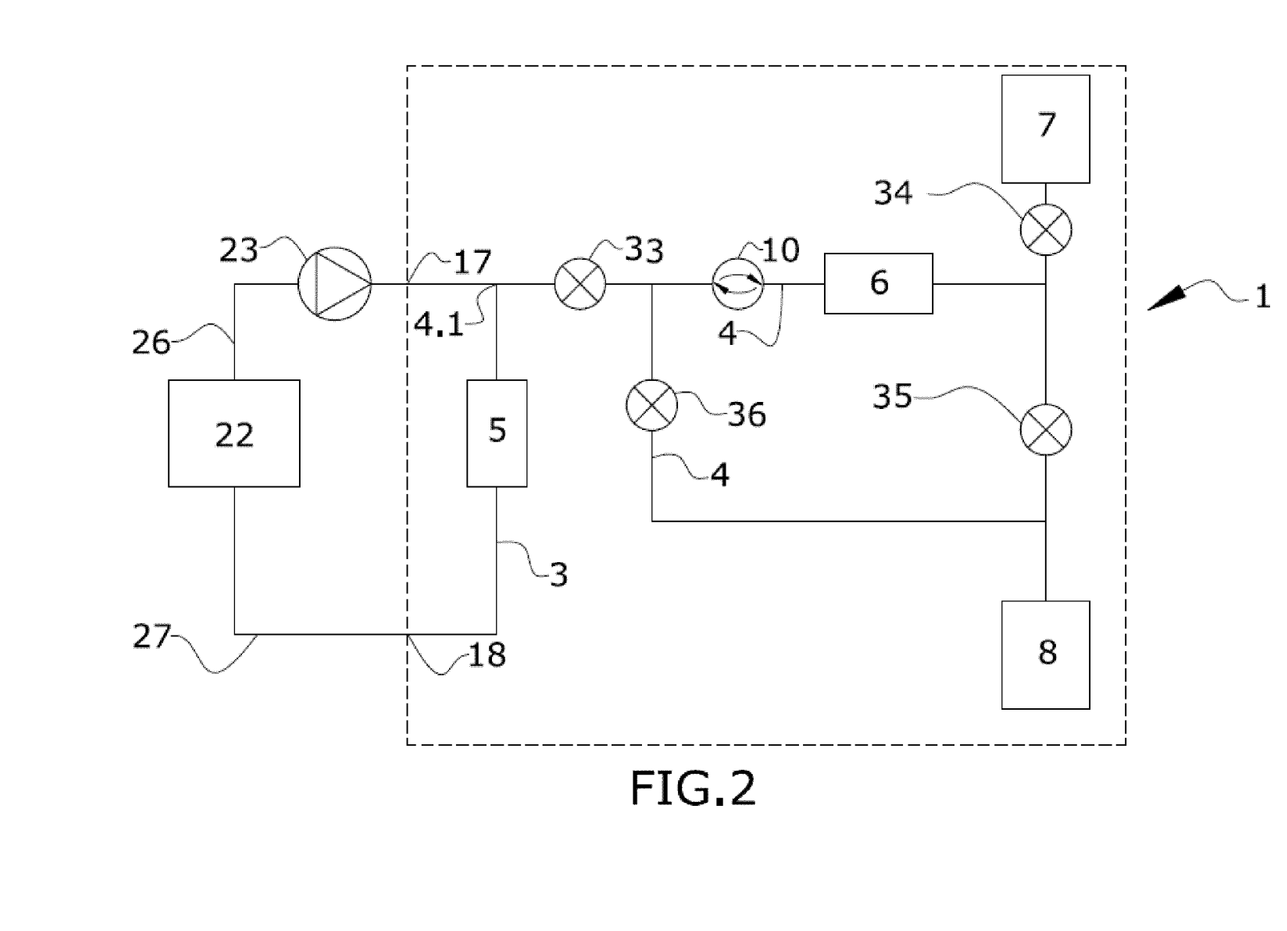
FIG. 2 illustrates a particular schematic example of the disposable cartridge according to another particular embodiment of the present invention.

FIGS. 1A-2 each schematically show a particular example of a disposable cartridge (1) (broken lines). The disposable cartridge (1) comprises a first duct (3) connected at one of the ends thereof to the fluid inlet (17) and connected at the other end to the fluid outlet (18). The manner in which the disposable cartridge (1) is directly connected with the fluid handling receptacle (22) through the outlet duct (26) and the inlet duct (27), which can be understood as a continuation or prolongation of the first duct (3), can be seen in these particular examples. The disposable cartridge (1) further comprises a first optical, pH, $O_2$, and/or $CO_2$ sensor (5) connected to this first duct (3).

The fluid inlet (17) and the fluid outlet (18) are understood as fluid connectors connecting with the main circuit, i.e., connecting directly with the fluid handling receptacle (22).

FIGS. 1A-2 furthermore show a disposable cartridge (1) comprising a second duct (4) connected to the first duct (3). Part of this second duct (4) is parallel to the first duct (3). The disposable cartridge (1) has a residue receptacle (8) connected to the second duct (4), a cleaning receptacle (7) also connected to the second duct (4), and a second glucose and/or lactate enzyme sensor (6) connected to the second duct (4) and arranged between the receptacles (7, 8).

In FIGS. 1A and 1B, the second duct (4) comprises three ends, a first end (4.1) connected to the first duct (3) so that the fluid entering the cartridge flows not only through the first duct (3) but also through the second duct (4). Furthermore, the cleaning receptacle (7) is connected to the second duct (4) at the second end (4.2) thereof, whereas the residue receptacle (8) is connected to the second duct (4) at the third end (4.3) thereof.

In this particular example, the cleaning receptacle (7) is fundamental for suitable operation of the second sensor (6) throughout the entire experimental work cycle.

FIG. 1A furthermore shows that the disposable cartridge (1) comprises a first pump (10) connected in the second duct (4) between the first end (4.1) thereof and the second sensor (6). This first pump (10) is in charge of circulating or driving the fluid entering through the first duct (3) to the disposable cartridge (1) through the duct network. Furthermore, the first pump (10) is in charge of pumping the fluid so that it flows through the second duct (4), passing through the second sensor (6), even until reaching the residue receptacle (8). The disposable cartridge (1) furthermore has a second pump (11) connected in the second duct (4) between the cleaning receptacle (7) and the second sensor (6). This second pump (11) is in charge of circulating or driving through the duct network the cleaning liquid coming from the cleaning receptacle (7), through the second duct (4), to the second sensor (6) and even reaching the residue receptacle (8). The first pump (10) and the second pump (11) of this particular example of disposable cartridge (1) are the flow control means for controlling the flow of fluid through the duct network, particularly through the second duct (4) according to this example.

FIG. 1A furthermore schematically shows a cell culture fluid handling receptacle (22) of a bioreactor, wherein the flow control means for controlling the flow of fluid entering and leaving the fluid handling receptacle (22) through the outlet duct (26) and inlet duct (27), respectively, are a pump (23) for driving inflow fluid in the system. Through this inflow fluid pump (23), the bioreactor installation works under perfusion conditions. In this particular example, the inflow fluid pump (23) is connected to the outlet duct (26) between the fluid handling receptacle (22) and the fluid inlet (17). Furthermore, this inflow fluid pump (23) is in charge of pumping or driving the fluid coming from the interior of the fluid handling receptacle (22) and circulating it or causing it to flow to the duct network of the disposable cartridge (1).

FIG. 1B shows an embodiment of the disposable cartridge (1) comprising a first valve (24) connected in the second duct (4) between the first end (4.1) thereof and the second sensor (6). This first valve (24) is in charge of regulating the passage of fluid entering the disposable cartridge (1) through the first duct (3) to the second duct (4). Furthermore, the first valve (24) is in charge of controlling the flow of fluid flowing through the second duct (4) to the second sensor (6) and the residue receptacle (8). The disposable cartridge (1) furthermore has a second valve (25) connected in the second duct (4) between the cleaning receptacle (7) and the second sensor (6). This second valve (25) is in charge of regulating the passage of cleaning liquid coming from the cleaning receptacle (7) to the second sensor (6) through the second duct (4). Furthermore, the cartridge (1) comprises a third pump (12) connected in the second duct (4) between the second sensor (6) and the residue receptacle (8). This third pump (12) is adapted for pumping from the first duct (3) to the second duct (4) and/or through the second sensor (6) to the residue receptacle (8)

FIG. 1B furthermore schematically shows a cell culture fluid handling receptacle (22) of a bioreactor, wherein the flow control means for controlling the flow of fluid entering and leaving the fluid handling receptacle (22) through the outlet duct (26) and inlet duct (27), respectively, are a pump (23) for driving inflow fluid in the system. Through this inflow fluid pump (23), the bioreactor installation works under perfusion conditions. In this particular example, the inflow fluid pump (23) is connected to the inlet duct (27) between the fluid handling receptacle (22) and the fluid outlet (18). Furthermore, this inflow fluid pump (23) is in charge of pumping or driving the fluid coming from the interior of the fluid handling receptacle (22) and circulating it or causing it to flow to the duct network of the disposable cartridge (1).

FIG. 2 furthermore shows that the disposable cartridge (1) comprises a first pump (10) connected to the second duct (4) between the first end (4.1) thereof and the second sensor (6). This first pump (10) is in charge of driving the fluid entering through the first duct (3) to the disposable cartridge (1), and is furthermore in charge of pumping the fluid so that it flows through the second duct (4), passing through the second sensor (6) even until reaching the residue receptacle (8). The disposable cartridge furthermore has four check valves (33, 34, 35, 36) connected to the second duct and configured for regulating the passage of fluid and/or cleaning liquid through the duct network. The manner in which the first check valve (33) would be in charge of regulating the passage of fluid from the first duct (3) to the second duct (4) is observed in particular. The second check valve (34) is in charge of regulating the passage of cleaning liquid through the second duct (4). The third check valve (35) and the fourth check valve (36) are in charge of regulating the passage of fluid and/or cleaning liquid through the second duct (4). In this particular example, the combination of a first pump (10) and the check valves (33, 34, 35, 36) form the flow control means for controlling the flow of fluid of the disposable cartridge (1) shown in FIG. 2. For this particular example, the first pump (10) is an alternating flow pump, i.e., advantageously, depending on the direction of turning of said pump, the fluid would move in one direction or another. In particular, if the first pump (10) turns in a first direction, the fluid circulating through the first duct (3) is pumped to the second duct (4), being delivered to the second sensor (6). However, if this first pump (10) turns in a second direction, the cleaning liquid would be pumped to the second sensor (6) so that it continues to circulate subsequently, or to the first duct (3), or to the residue receptacle (8). The preceding explanation of the direction the fluid would take along the second duct (4) would in turn be conditioned by each of the check valves.

The different tubes/ducts forming the duct network of the disposable cartridge (1) and the interconnection cables are not shown in FIGS. 3 to 9 in order to better understand the system.

Figure 3:
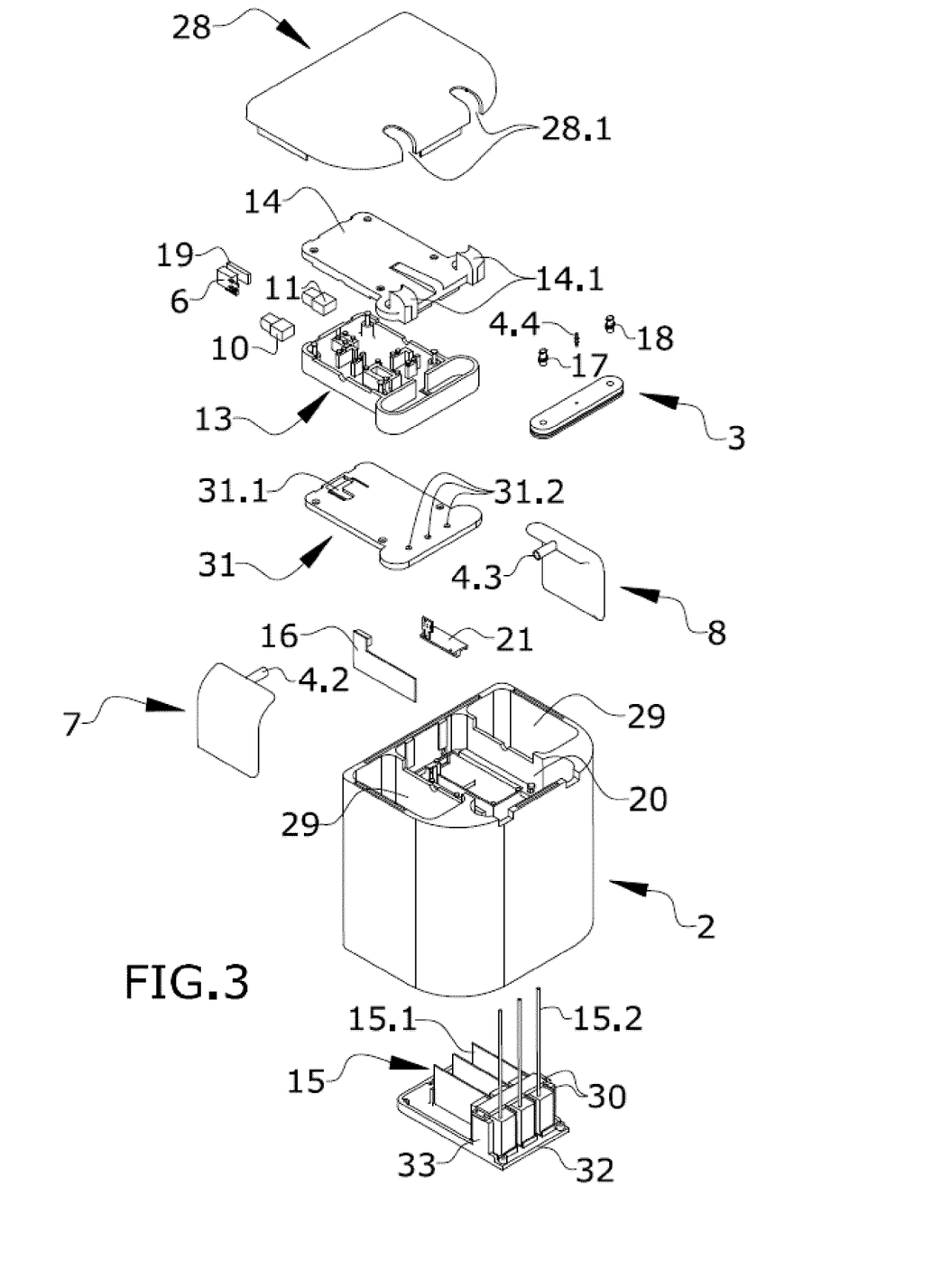
FIG. 3 shows an exploded perspective view of a system consisting of a disposable cartridge and platform according to a particular embodiment of the present invention.

FIG. 3 shows an exploded view of a system formed by the disposable cartridge (1) and the platform (2) and the different elements forming same. Starting from the top, the upper cover (28) of the platform (2) is shown, said cover comprising two holes (28.1) suitable for enabling access to the fluid inlet (17) and the fluid outlet (18) of the cartridge (1) when it is housed in the platform (2). The disposable cartridge (1) having a base structure (13) formed by different compartments in which the different elements forming the disposable cartridge (1) are housed is then shown. The elements of the cartridge (1) shown are, among others, the first duct (3) to which the elements are connected or in which the first sensor (5) is arranged (shown in FIGS. 7 and 8). This first duct (3) has at the ends thereof the fluid inlet (17) and the fluid outlet (18), respectively, and an intermediate connector (4.4) suitable for connecting the first duct (3) with the second duct (4) (not shown in the drawing). The fluid inlet (17) and the fluid outlet (18) can be understood as end connectors suitable for connecting the first duct (3) to the outlet duct (26) and the inlet duct (27) (which are understood as a continuation of the first duct (3)), these ducts (26, 27) being connected with a fluid handling receptacle (22) (not shown in the drawing). Furthermore, FIG. 3 shows the second sensor (6) in parallel with a pump connector (19) and a first pump (10) and a second pump (11), both also arranged in parallel. All these elements forming the disposable cartridge (1) are adapted for being integrated in the base structure (13) of said cartridge (1). The disposable cartridge furthermore has a cleaning receptacle (7) and a residue receptacle (8). Each receptacle (7, 8) is connected through the second end (4.2) and the third end (4.3) of the second duct (4), respectively, to the interior of the base structure (13).

Figure 4:
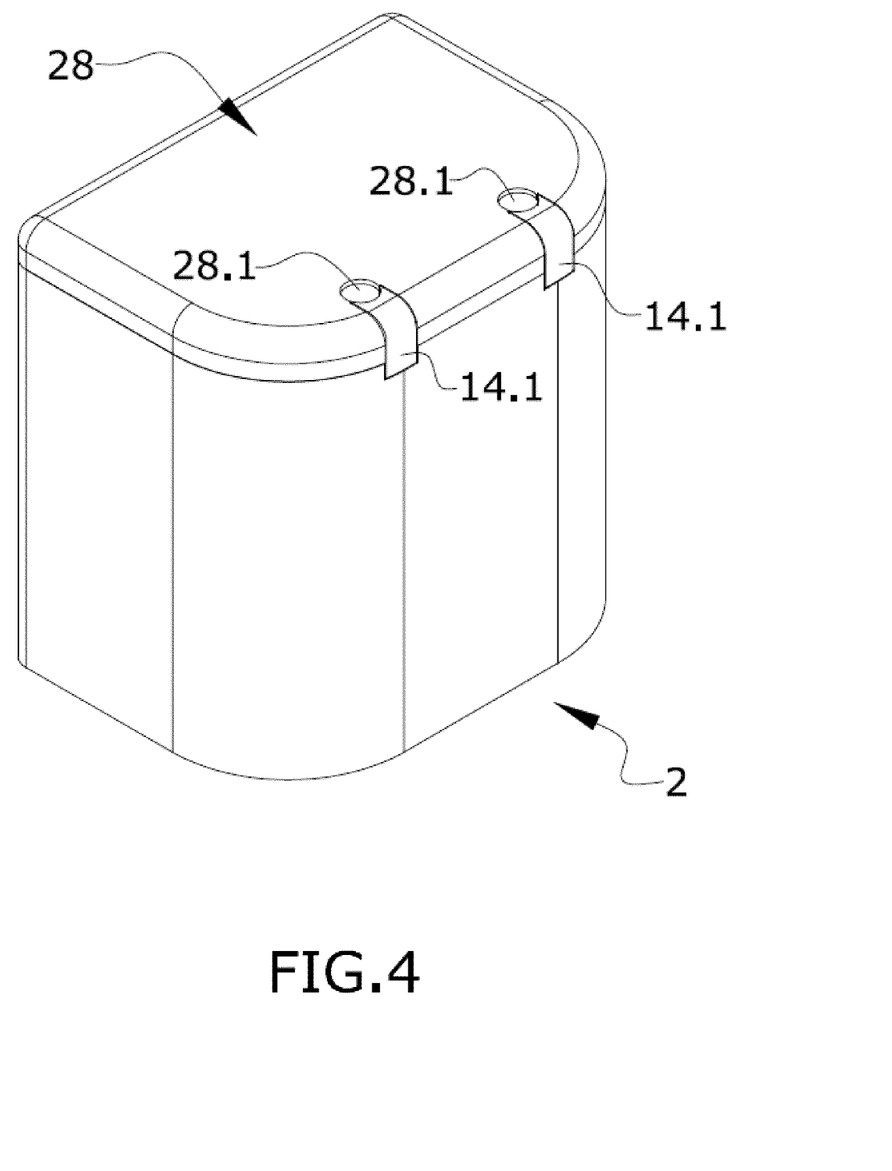
FIG. 4 shows a perspective view of the platform according to a particular embodiment of the present invention.

FIG. 3 furthermore shows a platform (2) having a central housing (20) suitable for housing therein the base structure (13) together with its cartridge cover (14) univocally. This cartridge cover (14) has two projections (14.1) protruding towards the platform upper cover (28) when the cartridge (1) is housed in the interior of said platform, such that with the holes (28.1) of the upper cover (28) and said projections (14.1) of the cover (14), a structure in which the fluid inlet (17) and the fluid outlet (18) of the cartridge (1) are housed is formed. The platform (2) furthermore has two side housings (29) suitable for housing the receptacles (7, 8) of the disposable cartridge (1) therein. The central housing of the cartridge (1) in the central housing or space (20) of the platform (2) allows automatic connection between the electronics existing in the platform (2) and the components present in the disposable cartridge (1). The fact that the receptacles (7, 8) of the cartridge being housed in a compartment other than that of the actual structure of the cartridge (1) allows these receptacles (7, 8) to rest on the platform, thereby preventing stresses and imbalances in the disposable cartridge (1). In another particular example, the receptacles (7, 8) of the cartridge (1) would be arranged on the cartridge cover (14) one after another, or one on top of the other, such that when the cartridge (1) is coupled to the platform (2), the receptacles (7, 8) would be arranged inside said platform (2) and covered by the upper cover (28) of the platform (2) (as shown in FIG. 4).

The platform (2) furthermore has housed therein, below where the cartridge (1) would be housed, second processing means (16) for connecting with the second sensor (6) of the cartridge (1) and interconnection means (21). In this particular example, the second processing means (16) and the interconnection means (21) are a printed circuit board. Both the second processing means (16) and the interconnection means (21) are located in the interior of the platform, below where the cartridge would be located and separated from said cartridge (1) through an inner cover (31). This inner cover (31) has at least a first opening (31.1) through which connection of the second processing means (16) and the interconnection means (21) with the disposable cartridge (1) is made.

The platform (2) furthermore has therein, in the lower part, first processing means (15) arranged on a lower cover (32). In a particular example, the first processing means (15) consist of optical fibers (15.2) aligned with the first sensor (5) of the cartridge (1), this alignment being fundamental for the correct measurement of said first sensor (5). In addition to the optical fibers (15.2), the processing means (15) comprise at least one printed circuit board (15.1). In this particular example, since the first sensor (5) is made up of an optical pH sensor, another optical $CO_2$ sensor and another optical $O_2$ sensor, each of said sensors connects with a printed circuit board (15.1) and an optical fiber (15.2) both arranged such that they are aligned with the corresponding sensor in the interior of the platform (2). These first processing means (15) are fixed in the interior of the platform (2) through a fixing structure (30).

In this particular example, the optical fibers (15.2) are adapted for going through the inner cover (31), through second grooves or openings (31.2), to thereby reach each sensor which forms the first sensor (5).

In this particular example, the communication between the platform (2) and the external electronic data treatment system is done by means of a USB connector located in the intermediate part of a rear enveloping shell of the platform (2). This USB connection has two functions; it provides power supply to the installation and connects all the components present in said installation for the control thereof by means of the external electronic data treatment system (computer).

FIG. 4 shows a platform (2) closed with its upper cover (28) and housing therein a disposable cartridge (1) (not shown in the drawing). The manner in which a housing or guide structure is formed for the fluid inlet (17) and the fluid outlet (18) of the cartridge (1) through the holes (28.1) of the upper cover (28) of the platform (2) and the projections (14.1) of the cover (14) of the cartridge (1) is furthermore shown.

Figure 5:
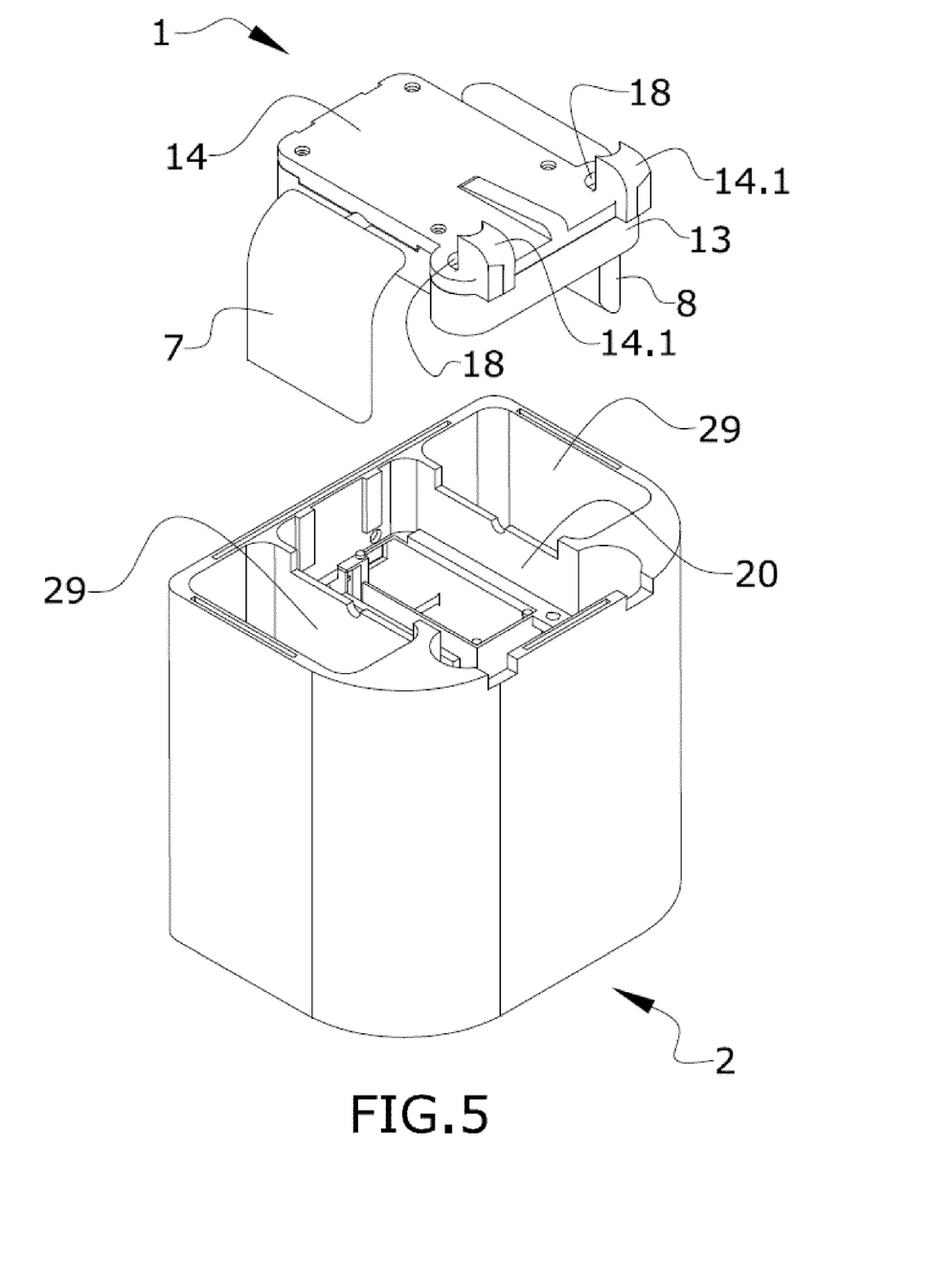
FIG. 5 illustrates a perspective view of the platform and disposable cartridge separately according to a particular embodiment of the present invention.

FIG. 5 shows an exploded view of the platform (2), and the disposable cartridge (1) is shown above in a position ready to be housed in the interior of the platform (2). The manner in which the base structure (13) covered by its cover (14) would fit into the central housing (20) of the platform (2) can be seen in this drawing. The manner in which the receptacles (7, 8) of the cartridge (1) each arranged on one side of the base structure (13) would be housed in the side housings (29) of the platform (2) can also be seen. In this configuration, the receptacles (7, 8) of the cartridge (1) could advantageously be connected and disconnected when it is located in the platform.

In a particular example, the base structure (13) together with the cover (14), forming the disposable cartridge (1), has external dimensions of 140×112 mm and a height of 29 mm. FIG. 5 shows the entire assembly of the disposable cartridge (1) completely closed.

Figure 6:
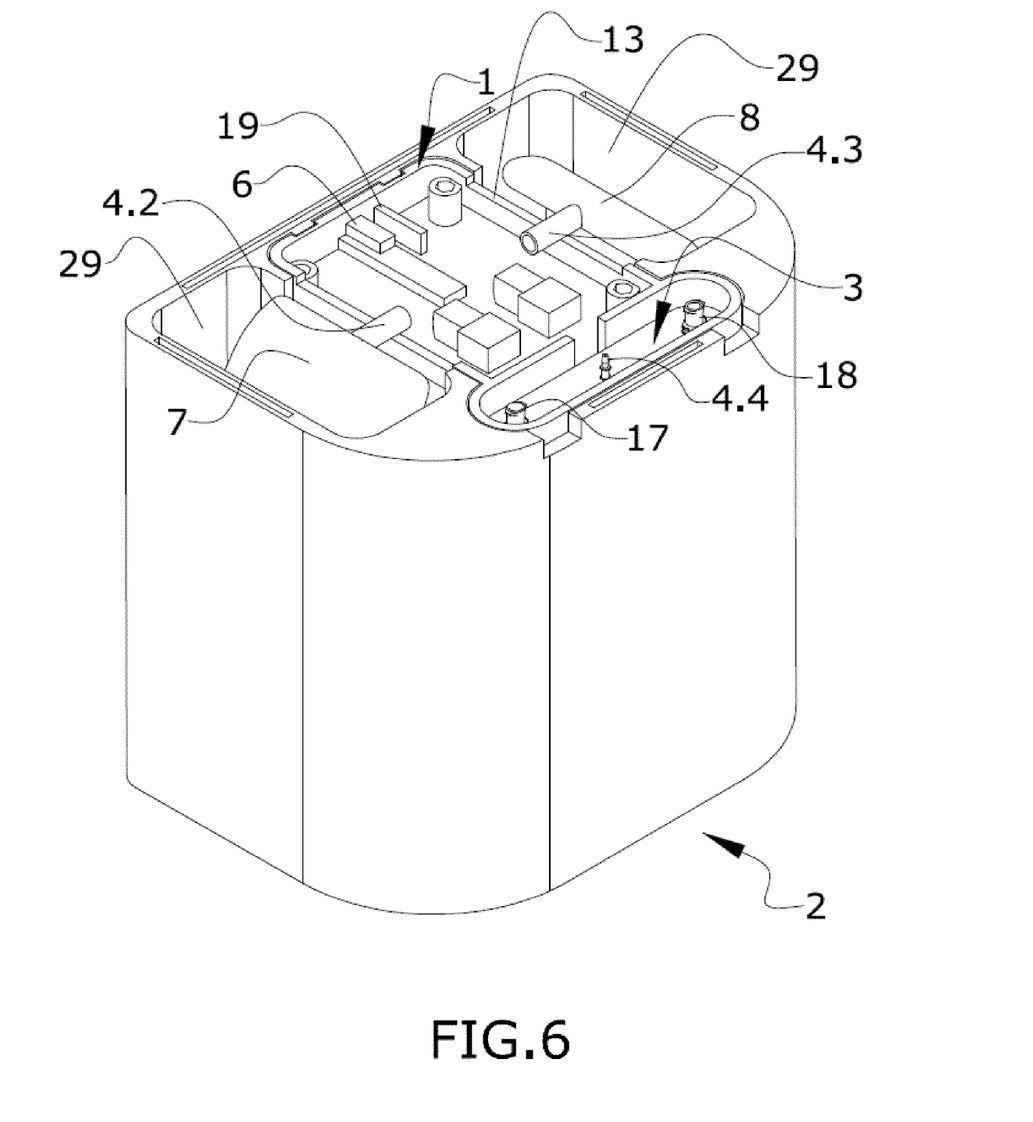
FIG. 6 shows the disposable cartridge housed in the platform according to an embodiment of the present invention.

FIG. 6 shows a top perspective view of the interior of the disposable cartridge (1) housed in the platform (2). The manner in which the cleaning receptacle (7) is located in the side housing (29) of the platform (2) and connected to the interior of the cartridge through the second end (4.2) of the second duct (4) (not shown) is shown in this drawing. The manner in which the residue receptacle (8) is located in the other side housing (29) of the platform (2) and connected to the interior of the cartridge (1) through the third end (4.3) of the second duct (4) (not shown) is also shown. The manner in which the first duct (3) has an intermediate connector through which the end (4.1) of the second duct (4) is connected to the first duct (3) (not shown in the drawing) is also shown in this drawing.

FIG. 6 furthermore shows how the base structure (13) of the disposable cartridge (1) integrates therein the fluid inlet (17) and the fluid outlet (18), the first sensor (5) (not shown in the drawing), the second sensor (6) in parallel with a pump connector (19), and a first pump (10) and a second pump (11) arranged parallel to one another (shown in FIG. 3).

In a particular example, the first duct (3) has a dead volume of 1.5 ml, the fluid inlet (17) and the fluid outlet (18) are female LUER connectors connecting with the fluid handling receptacle (22).

Figure 7:
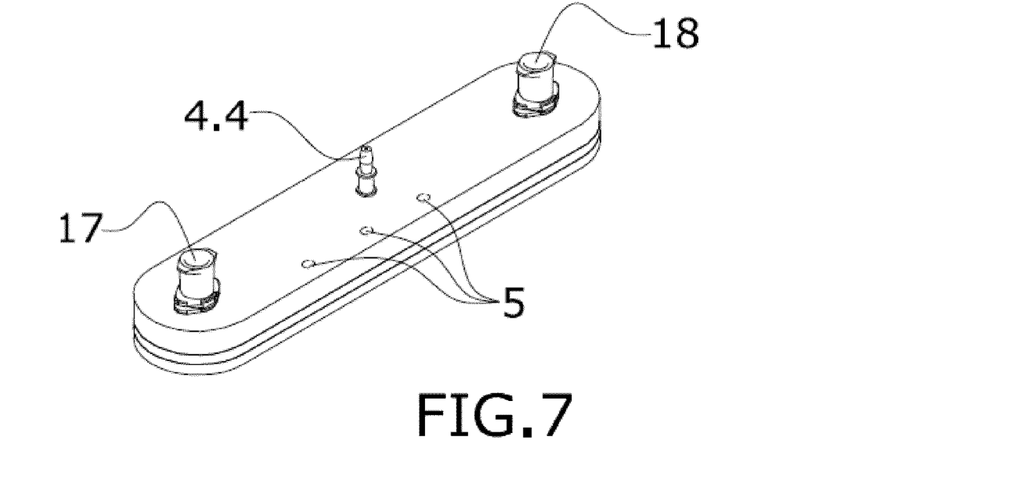
FIG. 7 shows a detailed perspective view of a duct of the disposable cartridge according to a particular embodiment of the present invention.

FIG. 7 shows the first duct (3) of the duct network, i.e., the duct through which the main flow of the disposable cartridge (1) circulates. The fluid sample coming from the fluid handling receptacle (22) (not shown) flows continuously through the first duct (3), this first duct (3) being used as a source of the samples needed for the purpose of taking measurements with the second sensor (6) arranged in the second duct (4) (not shown in FIG. 7) which is in fluid connection with the first duct (3). This second duct (4) would be connected to the first duct (3) through a first end (4.1) by means of an intermediate connector (4.4) shown in FIGS. 7 and 8.

Figure 8:
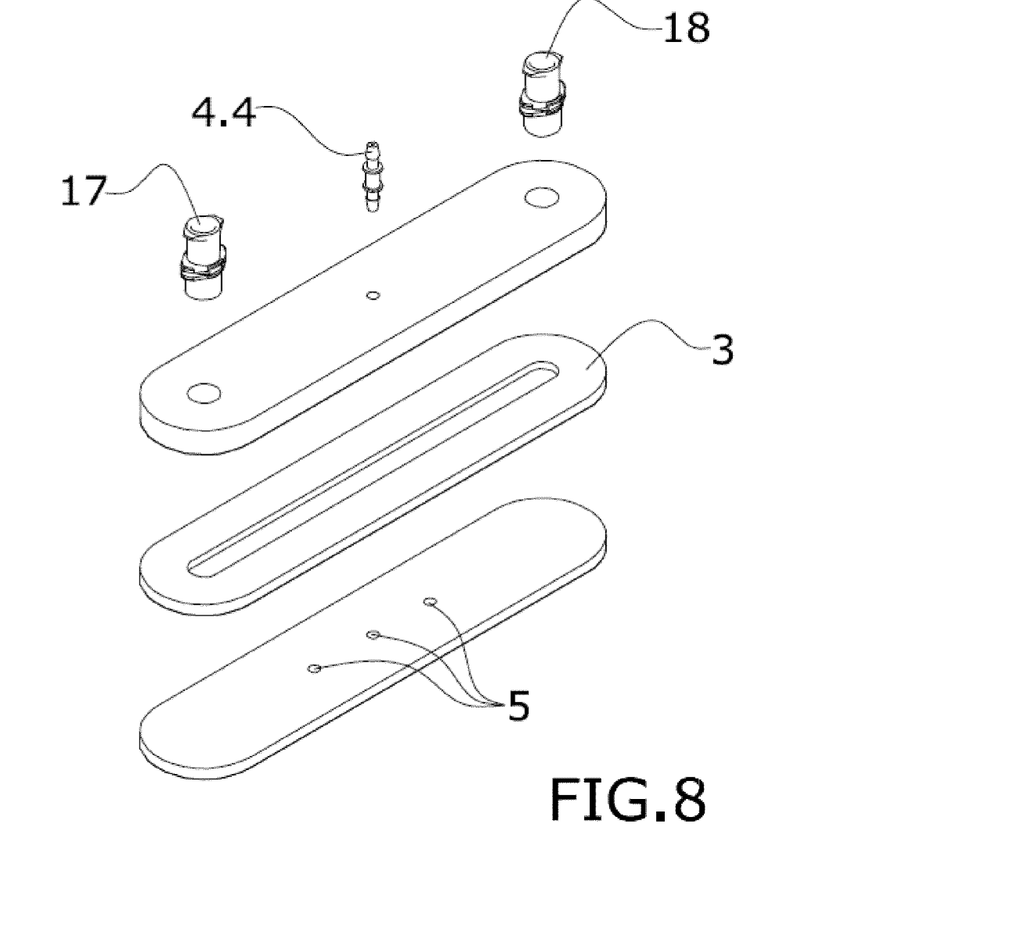
FIG. 8 shows an exploded perspective view of the components seen in FIG. 6.

FIGS. 7 and 8 show how the first duct (3) has a duct inlet (17) arranged at one of the ends thereof, through which fluid coming from the fluid handling receptacle (22) circulates to the interior of the disposable cartridge (1), and a duct outlet (18) arranged at another end, through which fluid coming from the first duct (3) circulates to the interior of the fluid handling receptacle (22). The duct inlet (17) and the duct outlet (18) are barb-type connectors.

FIG. 8 shows an exploded view of the first duct (3), showing in particular how the first sensor (5) is arranged in the lower part of the first duct (3), which sensor (5), in this particular example, is made up of three sensors, a pH sensor, another $CO_2$ sensor and another $O_2$ sensor. In a particular example, there would also be a temperature sensor connected to the first duct (3) that would be configured for connecting with processing means located in the platform (2) (not shown).

Figure 9:
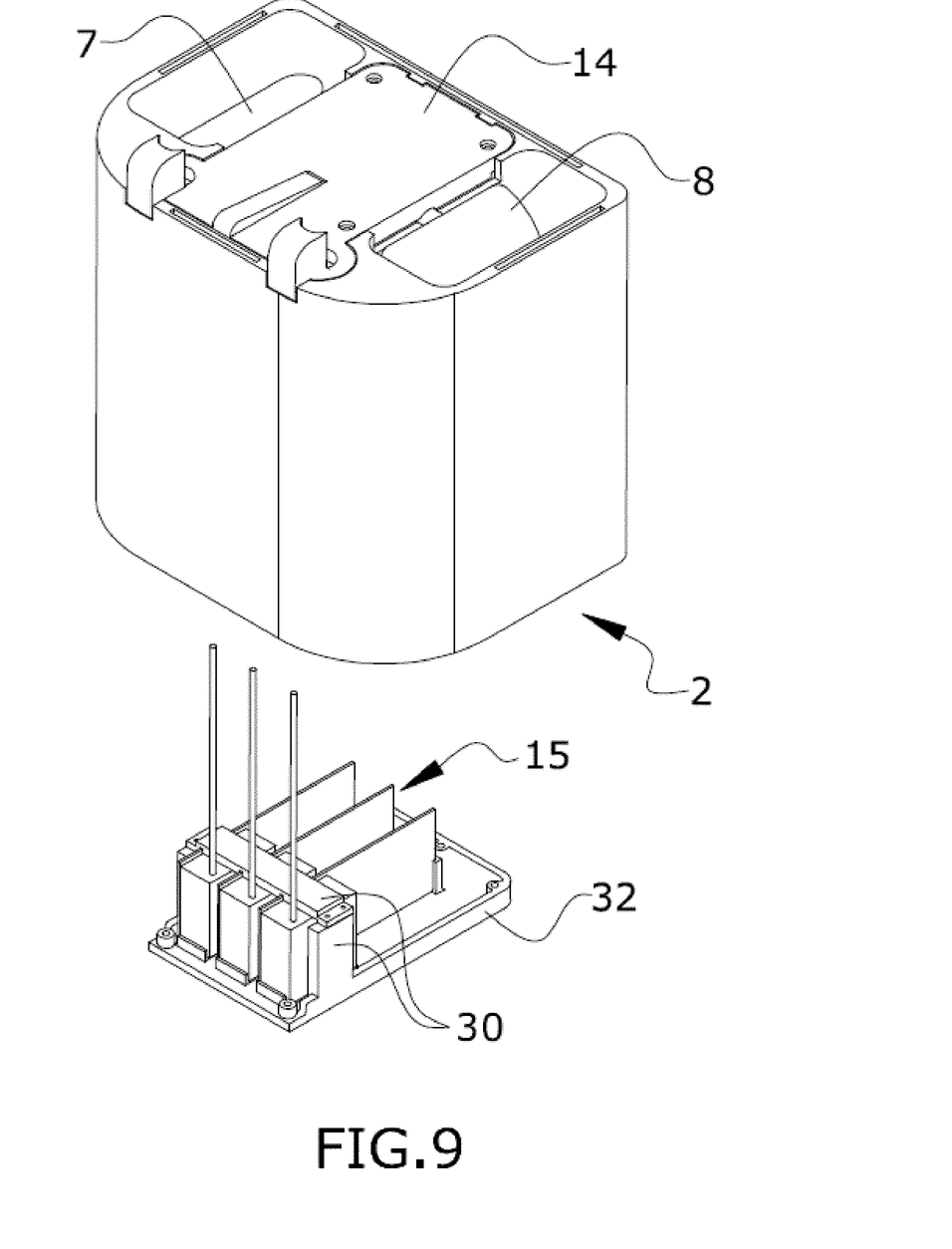
FIG. 9 shows a perspective view of the platform according to a particular embodiment of the present invention.

FIG. 9 shows an exploded view of the platform (2) integrating the disposable cartridge (1) inside the platform (2) and the first processing means (15) below the platform (2). This drawing furthermore shows the three optical fibers (15.2) corresponding with three printed circuit boards (15.1), respectively, and in particular, how these optical fibers (15.2) are arranged towards the interior of the platform indicating that they would connect with each of the sensors comprised in the first sensor (5) of the disposable cartridge (1) (not shown).

In a particular example, the platform (2) has external dimensions of 200×146 mm and a height of 190 mm. The platform (2) allows, on one hand, housing the disposable cartridge (1) in the upper part, and on the other hand, serving as a shell for accommodating therein all the non-disposable parts such as the optical fibers (15.2) and the control electronics.

Furthermore, FIG. 9 shows how the disposable cartridge (1) is housed in the interior of the platform (2) and has its cover (14). Each of the receptacles (7, 8) of this cartridge (1) is furthermore seen as being housed in a side housing (29) of the platform (2).

In a preferred illustrative embodiment as "embodiment 1", a disposable cartridge (1) for cooperating with a platform (2) for a system for monitoring and controlling the state of at least one fluid, preferably a cell culture, characterized in that it comprises:
  a duct network comprising at least one fluid inlet (17) and fluid outlet (18), this duct network being configured for circulating at least one fluid therein,
  a first sensor (5) connected to the duct network, the first sensor (5) being configured for measuring at least a first fluid parameter,
  a second sensor (6) connected to the duct network, the second sensor (6) being configured for measuring at least a second fluid parameter regardless of the first sensor (5), and
  flow control means for controlling the flow of fluid circulating through the duct network,
  wherein the first sensor (5) and second sensor (6) are respectively configured for connecting with at least one processing means (15, 16) of the platform (2).

"Embodiment 2". The disposable cartridge (1) according to "embodiment 1", characterized in that it comprises at least one receptacle connected to the duct network, the at least one receptacle being configured for housing fluids therein.

"Embodiment 3". The disposable cartridge (1) according to any of "embodiments" 1 to 2, characterized in that it comprises a residue receptacle (8) connected to the duct network, the residue receptacle (8) being configured for housing therein fluids coming from at least one of the sensors (5, 6), wherein the disposable cartridge (1) further comprises:
  a cleaning receptacle (7) connected to the duct network, the cleaning receptacle (7) being configured for releasing a cleaning liquid from its interior towards at least one of the sensors (5, 6) along the duct network, or
  a calibration receptacle connected to the duct network, the calibration receptacle being configured for housing therein calibration fluids that can be released along the duct network, or
  a combination of the above.

"Embodiment 4". The disposable cartridge (1) according to any of the preceding "embodiment", characterized in that the duct network comprises a plurality of ducts which are connected with one another and/or with the fluid inlet (17) and/or fluid outlet (18).

"Embodiment 5". The disposable cartridge (1) according to "embodiment 4", characterized in that the duct network comprises:
  a first duct (3) arranged between the fluid inlet (17) and the fluid outlet (18), and
  a second duct (4) configured for being in fluid communication with the fluid inlet (17),
  wherein the first sensor (5) is connected to the first duct (3), and the second sensor (6) is connected to the second duct (4).

"Embodiment 6". The disposable cartridge (1) according to "embodiment 5", characterized in that the second duct (4) is configured for being in fluid communication with the fluid inlet (17) through the first duct (3).

"Embodiment 7". The disposable cartridge (1) according to any of the preceding "embodiments", characterized in that the fluid flow control means comprise:
  at least one pump located in the duct network and adapted for controlling the flow of fluid circulating through the duct network, or
  at least one valve located in the duct network and configured for regulating the passage of fluid through the duct network, or
  a combination of the above.

"Embodiment 8". The disposable cartridge (1) according to any of the preceding "embodiments", characterized in that at least one of the sensors (5, 6) is an optical sensor.

"Embodiment 9". The disposable cartridge (1) according to "embodiment 8", characterized in that at least one of the sensors (5, 6) is an optical sensor for optical microscopy analysis.

"Embodiment 10". The disposable cartridge (1) according to any of "embodiments" 8 to 9, characterized in that at least one of the sensors (5, 6) is an optical pH, $O_2$ and/or $CO_2$ sensor.

"Embodiment 11". The disposable cartridge (1) according to any of the preceding "embodiments", characterized in that at least one of the sensors (5, 6) is an enzyme sensor.

"Embodiment 12". The disposable cartridge (1) according to "embodiment 11", characterized in that at least one of the sensors (5, 6) is a glucose, glutamine and/or lactate enzyme sensor.

"Embodiment 13". A platform (2) for cooperating with the disposable cartridge (1) of any one of "embodiments" 1 to 12 for a system for monitoring and controlling the state of at least one fluid, preferably a cell culture, the platform (2) being configured for being coupled with the disposable cartridge (1), characterized in that the platform (2) comprises:
- processing means (15, 16) configured for controlling at least the first sensor (5) and second sensor (6) of the disposable cartridge (1), respectively,
- interconnection means (21) adapted for centralizing the electrical connections of the sensors (5, 6) of the disposable cartridge (1), of at least one of the fluid flow control means and of an external electronic data treatment system.

"Embodiment 14". A system for monitoring and controlling the state of at least one fluid, preferably a cell culture, characterized in that it comprises:
- a disposable cartridge (1) according to any of "embodiments" 1 to 12, and
- a platform (2) according to "embodiment 13", wherein the disposable cartridge (1) cooperates with the platform (2) for monitoring and controlling the state of the at least one fluid.

"Embodiment 15". An installation for monitoring and controlling the state of the at least one fluid, preferably a cell culture, comprising:
- at least one fluid handling receptacle (22) adapted for handling therein fluids,
- a system according to "embodiment 14", and
- an external electronic data treatment system, wherein the electronic data treatment system is configured for treating data of the at least one of the sensors (5, 6) of the disposable cartridge (1) and furthermore for being connected to the interconnection means (21) of the platform (2) of the system; and wherein the inlet (17) and outlet (18) of the duct network of the disposable cartridge (1) of the system is configured for being in fluid communication with the interior of the fluid handling receptacle (22).

The invention claimed is:

1. A disposable cartridge configured for cooperating with a platform for monitoring and controlling the state of at least a cell culture located within a cell culture chamber arranged outside the disposable cartridge, characterized in that it comprises:
- a duct network comprising at least one fluid inlet and fluid outlet through which said duct network is configured to be in fluid communication with the interior of the cell culture chamber, this duct network being configured for circulating at least one fluid therein,
- a first sensor connected to the duct network, the first sensor being configured for measuring at least a first fluid parameter,
- a second sensor connected to the duct network, the second sensor being configured for measuring at least a second fluid parameter regardless of the first sensor, the second fluid parameter being different from the first fluid parameter, and
- flow control means for selectively controlling the flow of fluid circulating through the duct network towards the first sensor or the second sensor or both the first and second sensors, wherein
- the first sensor and second sensor are respectively configured for connecting with at least one processing means of the platform so that both first and second sensor control the state of at least one fluid coming from the cell culture chamber and circulating through the duct network,
- the fluid to be circulated in the duct network is a medium, or cells suspended in a medium, or a sample of any of the above, and the medium is a liquid medium and/or a culture medium,
- the disposable cartridge is configured to be directly connected with the cell culture chamber through an outlet duct connected to the fluid inlet and an inlet duct connected to the fluid outlet,
- the duct network comprises a first duct arranged between the fluid inlet and the fluid outlet, and a second duct configured for being in fluid communication with the fluid inlet, and
- the first sensor is connected to the first duct, and the second sensor is connected to the second duct.

2. The disposable cartridge according to claim 1, characterized in that it comprises at least one receptacle connected to the duct network, the at least one receptacle being configured for housing fluids therein.

3. The disposable cartridge according to claim 1, characterized in that it comprises a residue receptacle connected to the duct network, the residue receptacle being configured for housing therein fluids coming from at least one of the first and second sensors, wherein the disposable cartridge further comprises:
- a cleaning receptacle connected to the duct network, the cleaning receptacle being configured for releasing a cleaning liquid from its interior towards at least one of the first and second sensors along the duct network, or
- a calibration receptacle connected to the duct network, the calibration receptacle being configured for housing therein calibration fluids that can be released along the duct network, or
- a combination of the above.

4. The disposable cartridge according to claim 1, characterized in that the second duct is configured for being in fluid communication with the fluid inlet through the first duct.

5. The disposable cartridge according to claim 1, characterized in that the flow control means comprises:
- at least one pump located in the duct network and adapted for controlling the flow of fluid circulating through the duct network, or
- at least one valve located in the duct network and configured for regulating the passage of fluid through the duct network, or
- a combination of the above.

6. The disposable cartridge according to claim 1, characterized in that at least one of the first and second sensors is an optical sensor.

7. The disposable cartridge according to claim 6, characterized in that at least one of the first and second sensors is an optical sensor for optical microscopy analysis.

8. The disposable cartridge according to claim 6, characterized in that at least one of the first and second sensors is an optical pH, $O_2$ and/or $CO_2$ sensor.

9. The disposable cartridge according to claim 1, characterized in that at least one of the first and second sensors is an enzyme sensor.

10. The disposable cartridge according to claim 9, characterized in that at least one of the first and second sensors is a glucose, glutamine and/or lactate enzyme sensor.

\* \* \* \* \*